(12) United States Patent
Kuwabara

(10) Patent No.: US 6,650,769 B1
(45) Date of Patent: Nov. 18, 2003

(54) REVIEW STATION AND APPEARANCE INSPECTION DEVICE FOR CHECKING SEMICONDUCTOR WAFERS

(75) Inventor: Masayuki Kuwabara, Machida (JP)

(73) Assignee: Tokyo Seimitsu Co., Ltd., Tokyo (JP)

( * ) Notice: Subject to any disclaimer, the term of this patent is extended or adjusted under 35 U.S.C. 154(b) by 0 days.

(21) Appl. No.: 09/379,171

(22) Filed: Aug. 23, 1999

(30) Foreign Application Priority Data

Nov. 26, 1998 (JP) ............................................. 10-335429

(51) Int. Cl.[7] ................................................ G06K 9/00
(52) U.S. Cl. .................. 382/149; 382/297; 250/559.37; 356/237.1; 356/614
(58) Field of Search ................................ 382/149, 144, 382/154, 141, 151, 294, 297, 106; 250/559.44, 559.37; 356/614, 399, 401, 124, 239.2, 237.5, 237.1

(56) References Cited

U.S. PATENT DOCUMENTS

| | | | | |
|---|---|---|---|---|
| 3,898,617 A | * | 8/1975 | Kashioka et al. | 328/151 |
| 4,330,775 A | * | 5/1982 | Iwamoto et al. | 382/141 |
| 4,547,895 A | * | 10/1985 | Mita et al. | 382/144 |
| 4,556,317 A | * | 12/1985 | Sandland et al. | 356/237.1 |
| 4,573,791 A | * | 3/1986 | Phillips | 355/77 |
| 4,768,883 A | * | 9/1988 | Waldo et al. | 356/399 |
| 4,858,157 A | * | 8/1989 | Murai et al. | 382/154 |
| 5,381,004 A | * | 1/1995 | Uritsky et al. | 250/307 |
| 5,574,556 A | * | 11/1996 | Mori et al. | 356/244 |
| 5,847,822 A | * | 12/1998 | Sugiura et al. | 356/239.2 |
| 6,051,845 A | * | 4/2000 | Uritsky | 250/559.3 |

FOREIGN PATENT DOCUMENTS

JP    01-152634    *  6/1989

* cited by examiner

Primary Examiner—Jayanti K. Patel
Assistant Examiner—Sheela Chawan
(74) Attorney, Agent, or Firm—Christie, Parker & Hale, LLP

(57) ABSTRACT

A review station comprising a wafer chuck capable of turning by at least 270 degrees, and an X-Y stage that moves over a distance one-half the diameter of a semiconductor wafer. Each of four regions obtained by dividing the surface of the semiconductor wafer 1 into four areas are successively observed using a stationary microscope 2 by turning the wafer chuck depending upon the coordinates of defective positions of the wafer to review the defects on the whole surface of the wafer.

4 Claims, 3 Drawing Sheets

(Prior art)

REVIEW STATION AND APPEARANCE INSPECTION DEVICE FOR CHECKING SEMICONDUCTOR WAFERS

BACKGROUND OF THE INVENTION

1. Field of the Invention

The present invention relates to a review station and an appearance inspection device for inspecting defects in semiconductor wafers.

2. Description of the Related Art

In a conventional review station for semiconductor wafers, the wafer is placed on a chuck on the X-Y stage which is moved in the X-direction and in the Y-direction according to coordinates of defective positions obtained by an appearance inspection device, and the defects are brought into a visual field of a microscope secured to an upper part of the station over the stage to review the defects.

It is, however, a recent trend to increase the size of the wafer in order to enhance the production efficiency by producing an increased number of semiconductor chips from a single wafer. Nowadays, wafers of a size in excess of 12 inches (about 300 mm) have been supplied. To observe the whole surface of the wafer 1 by moving the conventional X-Y stage in the X-direction and Y-direction only as shown in FIG. 3, however, requires a wafer-moving region (A), described by a circle of a radius of 300 mm with the objective of a microscope 2 as a center, when a wafer of a size of 12 inches is to be handled. The size of the stage unit becomes not smaller than 600 mm in the direction of depth and in the lateral direction, respectively, causing the whole device to become very bulky. Besides, the axes of the X-Y stages must cover a moving range at least equal to the diameter (D) of the wafer. Therefore, the stage must have an increased rigidity with an increase in the diameter of the wafer.

Even in the case of an appearance inspection device in which the wafer placed on the X-Y stage is continuously scanned in the X-direction by an image pick-up unit of a combination of an optical microscope and an imaging element such as a TDI while moving the position of the wafer in the Y-direction by the width of scanning, and the obtained image is successively compared among the dies to inspect defects in the wafer, it is required to provide a range for moving the X-Y stage as for the above-mentioned review station and, besides, precision of the stage decreases with an increase in the moving distance. Moreover, the stage in the appearance inspection device requires precision of a level much higher than that of the precision required for the review station, driving up the cost in proportion to an increase in the diameter of the wafer.

As described above, it is becoming more difficult to cope with an increase in the diameter of the wafer as an extension of the prior art.

SUMMARY OF THE INVENTION

The present invention was accomplished in view of the problems inherent in the above-mentioned prior art, and its object is to provide a review station and an appearance inspection device for checking semiconductor wafers without increasing the size of the whole inspection device despite an increase in the diameter of the semiconductor wafer, suppressing the moving range of the stage to be not larger than the radius of the wafer in at least one axis, and suppressing a drop in the precision of the stage.

A review station according to an embodiment of the present invention has a wafer chuck that is allowed to turn by at least 270 degrees and an X-Y stage which moves over a distance one-half the diameter of the semiconductor wafer, wherein the regions obtained by dividing the surface of the semiconductor wafer into four areas are successively observed to review the defects on the whole surface of the wafer, and the mechanism needs to move the X-Y stage only over a distance equal to the radius of the wafer compared with the moving distance of the conventional device, making it possible to decrease the size of the device as a whole. Furthermore, the moving amount of the stage is halved and the precision of the stage is highly enhanced.

According to the review station of the present invention, furthermore, the regions obtained by dividing the surface of the semiconductor wafer into two areas are successively observed to review the defects on the whole surface of the wafer.

An appearance inspection device according to another embodiment of the present invention has a wafer chuck allowed to turn by at least 180 degrees, an X-stage which moves over a distance at least equal to the diameter of the wafer, and a Y-stage which moves over a distance at least one-half the diameter of the wafer, wherein the semiconductor wafer is scanned as two half circles, and the lateral width is decreased by an amount equal to the reduction of the moving distance of the Y-stage by half.

The present invention may be more fully understood from the description of preferred embodiments of the invention set forth below together with the accompanying drawings.

DESCRIPTION OF THE PREFERRED EMBODIMENTS

Figure 1:
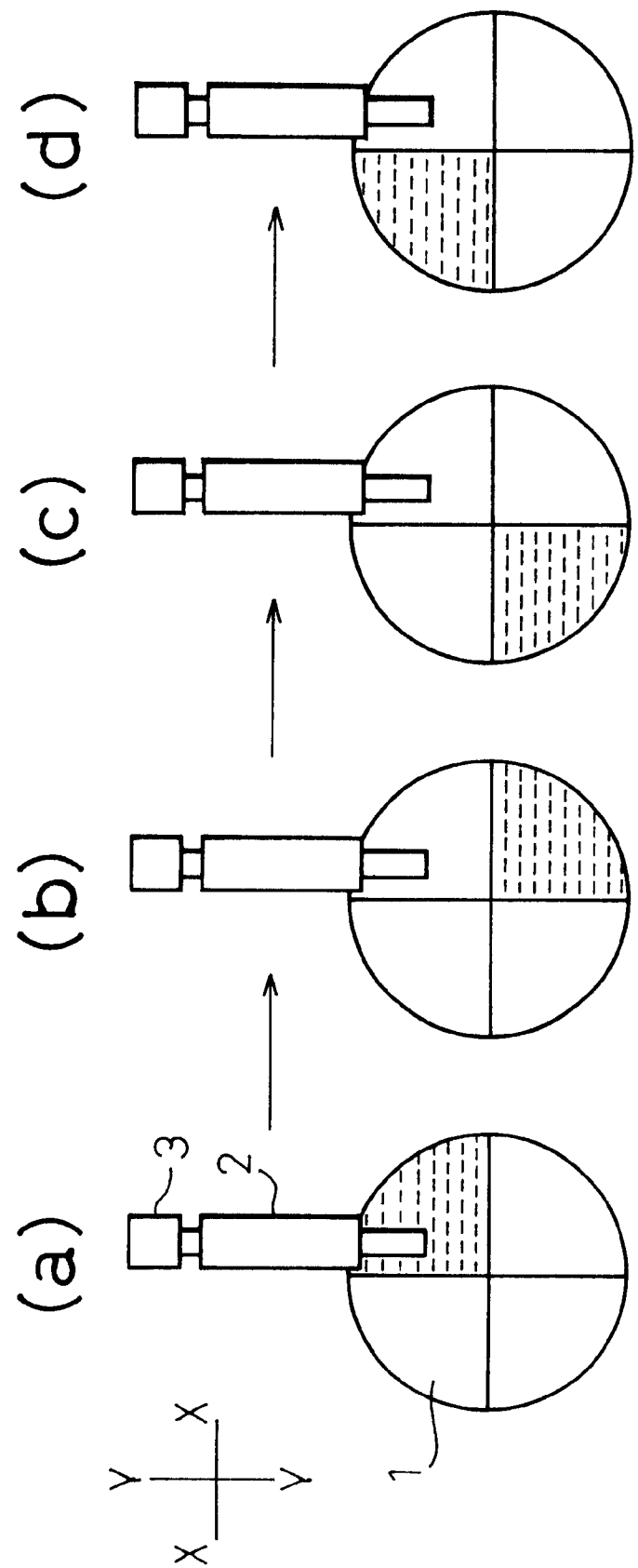
FIG. 1 including FIGS. 1(a) through and including 1(d), is a diagram illustrating a procedure for reviewing the defects on the whole surface of a wafer by successively observing the regions obtained by dividing the surface of the semiconductor wafer into four areas in a review station according to a first embodiment of the present invention.

Reviewing defect using the review station according to a first embodiment of the present invention will now be described with reference to FIG. 1.

FIGS. 1(a), 1(b), 1(c) and 1(d) illustrate a procedure in which the semiconductor wafer is divided into four regions, each region is reviewed for defects, then, the semiconductor wafer is turned by 90 degrees to continuously review for the defects in the next region to finally review the whole surface of the semiconductor wafer. In FIG. 1, reference numeral 1 denotes a semiconductor wafer, 2 denotes a microscope secured to a portion over the semiconductor wafer, and 3 denotes a camera mounted on the microscope.

The X-Y stage is supported in a review station body, not shown, by using, for example, a linear ball bearing mechanism. Furthermore, a chuck (not shown) for the semiconductor wafer is provided on the X-Y stage. The X-Y stage moves over a range of from the outermost circumference of the semiconductor wafer to a position slightly traversing over the center of rotation of the wafer chuck. Therefore, a moving mechanism such as a linear ball bearing for the X-Y stage needs to move over a shorter distance, about the radius of the semiconductor wafer, than the moving distance of the conventional device.

Next, described below with reference to FIG. 1 is the procedure for practically reviewing the defects by using the above-mentioned review station.

A defect coordinate file of a semiconductor wafer obtained from an appearance inspection device is received, and the defects are grouped into one of four regions depending upon the coordinate positions. The four groups include a fan-shaped region of from 0 degree to 90 degrees with the center of the semiconductor wafer as an origin, a fan-shaped region of from 90 degrees to 180 degrees, a fan-shaped region of from 180 degrees to 270 degrees, and a fan-shaped region of from 270 degrees to 360 degrees.

Next, the semiconductor wafer is aligned by using patterns such as of edges of dies present on the first fan-shaped region. After the alignment has been finished, defects existing in this regions are successively brought into the visual field of the microscope by using the X-Y stage as shown in FIG. 1(a) to observe the defects. After the defects have all been observed, the wafer chuck is turned by 90 degrees as shown in FIG. 1(b), the coordinates of defects are transformed accompanying the turn, and the defects belonging to the next fan-shaped region are reviewed in the same manner as described above.

When the stage has poor positional precision or poor rotational precision, the alignment may be deviated after every turn of the semiconductor wafer. However, since the alignment has been executed already by using patterns existing in the first fan-shaped region, rotational error only may be corrected. Even when the stage has a poor precision, addition of another alignment point suffices for the need. When the stage has a high degree of precision, the defects can be reviewed without at all affecting the speed.

Figure 2:
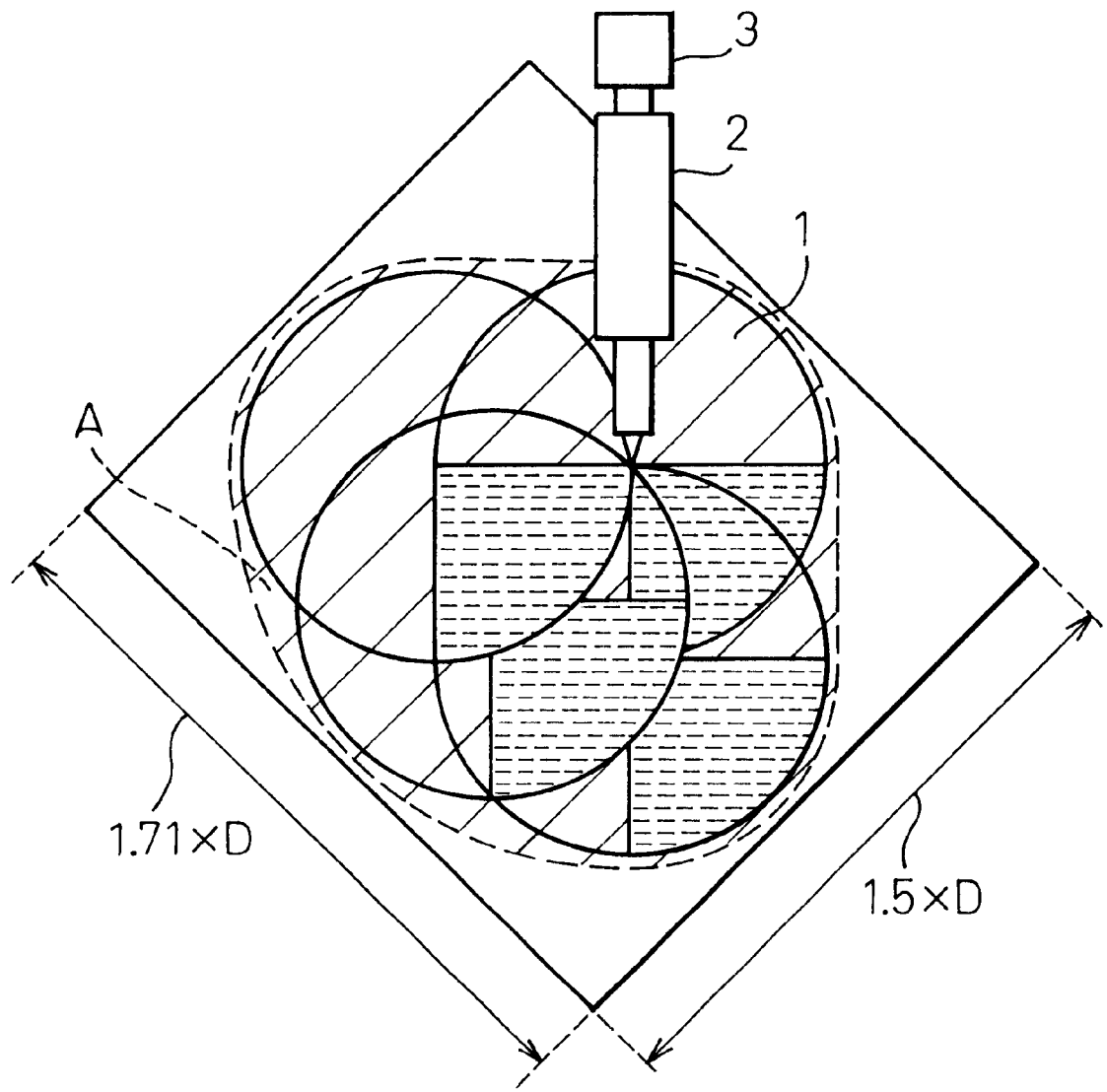
FIG. 2 is a diagram illustrating a moving region of the wafer of when the regions obtained by dividing the surface of the semiconductor wafer into four areas are successively observed in the review station according to the first embodiment of the present invention.
Figure 3:
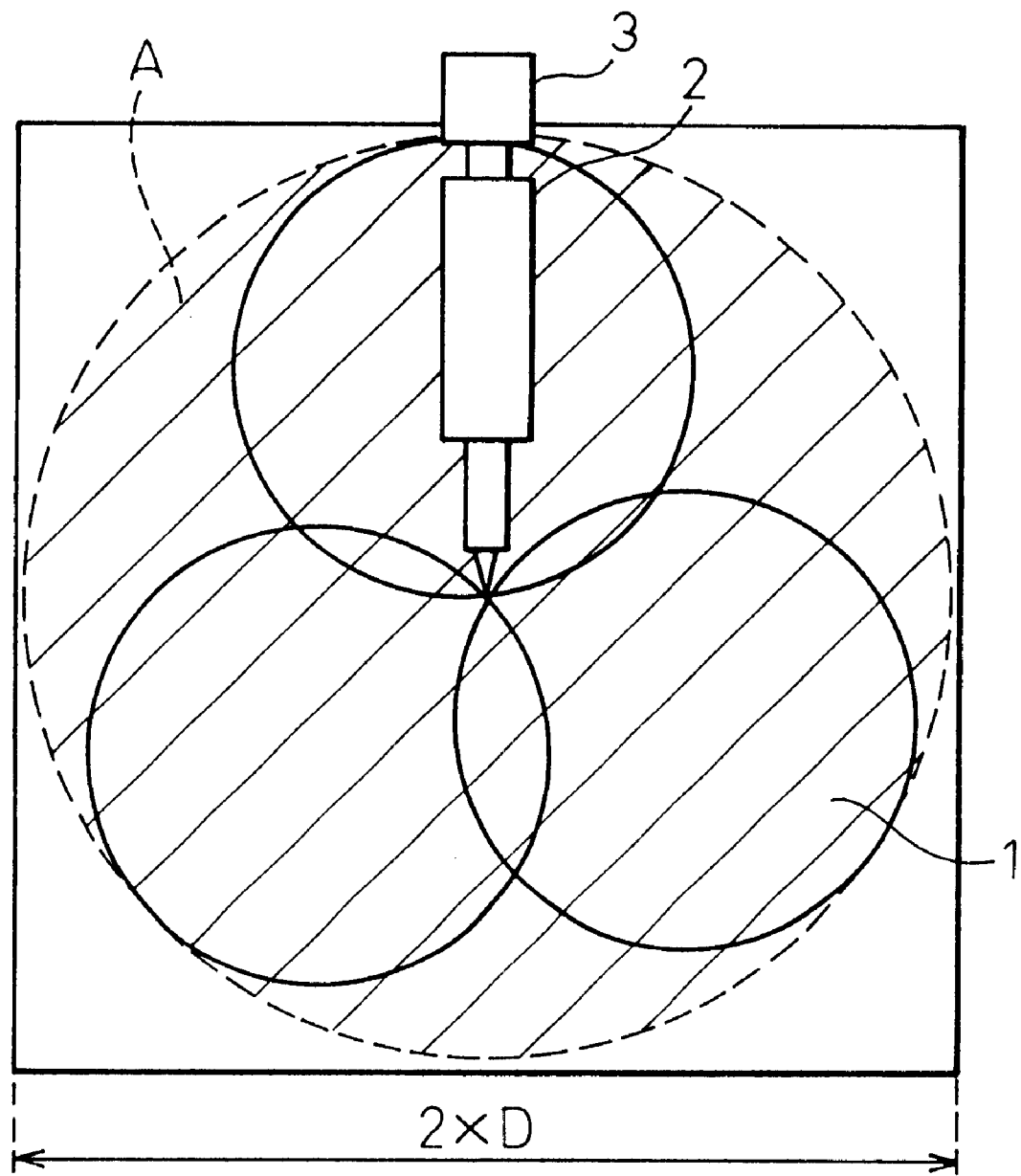
FIG. 3 is a diagram illustrating a moving region of the semiconductor wafer in a conventional device.

The same operation is repeated for all fan-shaped regions (FIGS. 1(a) to 1(d)) to review the defects on the whole surface of the semiconductor wafer. FIG. 2 illustrates a moving region of the wafer moved by the above-mentioned operation, wherein symbol D denotes the diameter of the wafer.

The first embodiment of the present invention has dealt with the case where the surface was divided into four fan-shaped regions. However, the whole surface of the semiconductor wafer can be observed by the same operation as the one described above even when the surface is observed by being divided into two half circles of from 0 degree to 180 degrees and from 180 degrees to 360 degrees.

The constitution in this case may be such that the wafer chuck may be turned by 180 degrees, and the X-Y stage may be moved in one direction by only the amount equal to the radius of the semiconductor wafer.

In this case, the size of the device can be decreased in either the direction of depth or the lateral direction only. In semiconductor plants, it is generally demanded to decrease the size in the lateral direction. When the device is installed penetrating through the wall, in particular, the size in the direction of depth is not much of a problem in many cases.

When the alignment must be executed again upon turning the semiconductor wafer, the alignment needs be executed twice for a piece of semiconductor wafer, and the extra time needed in addition to reviewing the defects can be shortened compared with when the semiconductor wafer is turned by 90 degrees each time.

The device for inspecting the appearance of the semiconductor wafer according to a second embodiment of the present invention has an X-stage that moves over a distance at least equal to the diameter of the semiconductor wafer, a Y-stage that moves over a distance at least one-half the diameter of the semiconductor wafer, and a wafer chuck provided on the X-Y stage to turn by at least 180 degrees.

Like an ordinary scanning-type appearance inspection device, the device for inspecting the appearance of the semiconductor wafers of the present invention starts the scanning from an end of the semiconductor wafer, turns the semiconductor wafer by 180 degrees after the inspection has finished for a half circle, and inspects the remaining half circle.

According to the conventional appearance inspection device, the moving range of the wafer is 2D×2D. According to the appearance inspection device of the present invention, the moving range of the wafer is 2D×1.5D, making it possible to decrease the size of the device.

It is also possible to reverse the moving distances of the x-stage and the Y-stage, as a matter of course.

According to the present invention, the device for inspecting the appearance of the semiconductor wafers is constituted as described above because of the reasons mentioned below.

In the appearance inspection device which receives the image upon scanning the semiconductor wafer and inspects the defects on the semiconductor wafers by comparing the images for every die, it is a generally accepted practice to scan the same row of dies or the same column of dies from one end to the other end of the semiconductor wafer. This is because some problems arise when the method of dividing the surface into the above-mentioned four fan-shaped regions is adapted to the appearance inspection device. Namely, the alignment for inspecting the appearance requires precision much higher than that of reviewing the defects, and the alignment must be completely executed four times, requiring a lot of extra time in addition to the inspection. In comparing the dies existing around the semiconductor wafers, furthermore, it may become difficult to maintain a sufficient number of dies for comparison. By taking these problems into consideration, the scanning method which is considered to be most efficient in the appearance inspection device is to inspect the semiconductor wafer by dividing it into two half circles.

According to the review station and the appearance inspection device of the present invention as described above in detail, the regions obtained by dividing the surface of the semiconductor wafer into four or into two are successively observed to review the defects or to inspect the appearance on the whole surface of the semiconductor wafer. It is, therefore, allowed to shorten the moving amount of the X-Y stage compared to that of the prior art and, hence, to decrease the size of the review station and of the appearance inspection device. A reduction in the moving amount of the X-Y stage means that a high degree of precision is obtained compared with that of the prior art, to handle the semiconductor wafers having increased diameters without permitting a drop in the precision.

While the invention has been described by reference to specific embodiments chosen for purposes of illustration, it should be apparent that numerous modifications could be made thereto by those skilled in the art without departing from the basic concept and scope of the invention.

What is claimed is:

1. An optical review station for reviewing defects by bringing the defects into a visual field of a fixed microscope by successively moving a semiconductor wafer in the X-Y directions based on the coordinates of defective positions of the semiconductor wafer obtained by using an appearance inspection device, comprising a wafer chuck allowed to turn by at least 270 degrees and an X-Y stage which moves over a moving range equal to one-half the diameter of said semiconductor wafer, wherein said wafer chuck is suitably turned by 90 degrees, 180 degrees or 270 degrees and said X-Y stage is moved in the X-direction and in the Y-direction depending upon the coordinates of defective positions of said semiconductor wafer to allow reviewing all of the defective positions of said semiconductor wafer.

2. The optical review station of claim 1, wherein the said wafer chuck is capable of rotating by 90 degrees, 180 degrees, and 270 degrees.

3. An optical review station for reviewing defects by bringing the defects into a visual field of a fixed microscope by successively moving a semiconductor wafer in the X-Y directions based on the coordinates of defective positions of the semiconductor wafer obtained by using an appearance inspection device, comprising a wafer chuck allowed to turn by at least 180 degrees and an X-Y stage which moves only in either the X-direction or the Y-direction over a distance equal to one-half the diameter of said semiconductor wafer, wherein said wafer chuck is suitably turned by 180 degrees and said X-Y stage is moved depending upon the coordinates of defective positions of said semiconductor wafer to allow reviewing all of the defective positions of said semiconductor wafer.

4. An appearance inspection device, for detecting defects on a surface of a semiconductor wafer by taking in an image by scanning the semiconductor wafer and comparing the images for every die or cell, comprising a wafer chuck allowed to turn by at least 180 degrees, an X-stage that is capable of moving over a distance equal to the diameter of said semiconductor wafer, and a Y-stage that is capable of moving over a distance equal to one-half the diameter of said semiconductor wafer, wherein said wafer chuck is suitably turned by 180 degrees and said X-stage and Y-stage are moved depending upon the scanning positions of said semiconductor wafer to allow inspections of the whole said surface of said semiconductor wafer.

* * * * *